(12) United States Patent
Forsell

(10) Patent No.: US 8,911,503 B2
(45) Date of Patent: Dec. 16, 2014

(54) HIP JOINT DEVICE, SYSTEM AND METHOD

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/383,309

(22) PCT Filed: Jul. 12, 2010

(86) PCT No.: PCT/SE2010/050820
§ 371 (c)(1),
(2), (4) Date: Jan. 10, 2012

(87) PCT Pub. No.: WO2011/005201
PCT Pub. Date: Jan. 13, 2011

(65) Prior Publication Data
US 2012/0109329 A1     May 3, 2012

Related U.S. Application Data

(60) Provisional application No. 61/229,738, filed on Jul. 30, 2009, provisional application No. 61/229,755, (Continued)

(30) Foreign Application Priority Data

| Jul. 10, 2009 | (SE) | 0900957 |
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |

(51) Int. Cl.
*A61F 2/34*     (2006.01)
(Continued)

(52) U.S. Cl.
CPC ............... *A61F 2/30756* (2013.01); *A61F 2/34* (2013.01); *A61F 2/3609* (2013.01);
(Continued)

(58) Field of Classification Search
CPC ................................................ A61F 2/28
USPC ............ 623/11.11, 14.12, 16.11–17.12, 22.11
See application file for complete search history.

(56) References Cited

U.S. PATENT DOCUMENTS

| 4,318,191 A | 3/1982 | Tepic |
| 5,344,459 A * | 9/1994 | Swartz ........................ 623/14.12 |

(Continued)

OTHER PUBLICATIONS

International Search Report for PCT/SE2010/050820, mailed Nov. 17, 2010.

*Primary Examiner* — Jason-Dennis Stewart

(57) ABSTRACT

A medical device, system, and method for treating hip joint osteoarthritis by providing a hip joint surface is provided. The hip joint comprising an acetabulum, being a part of the pelvic bone, comprising an acetabulum surface, and a caput femur, being a part of the femoral bone, comprising a caput femur surface. The medical device comprises a first sealing member adapted to be placed in the hip joint for creating a hollow space together with; the acetabulum, or an artificial replacement therefor, and the caput femur, or an artificial replacement therefor. The first sealing member is further adapted to have a shape adapted to seal the hollow space for receiving, within the hollow space, a material for resurfacing at least one of the acetabulum surface and the caput femur surface.

19 Claims, 13 Drawing Sheets

Related U.S. Application Data filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(51) Int. Cl.
*A61F 2/30* (2006.01)
*A61F 2/36* (2006.01)
*A61F 2/32* (2006.01)
*A61B 17/16* (2006.01)
*A61B 17/68* (2006.01)
*A61B 17/88* (2006.01)

(52) U.S. Cl.
CPC ......... *A61F 2002/30497* (2013.01); *A61F 2/32* (2013.01); *A61F 2002/30062* (2013.01); *A61F 2002/302* (2013.01); *A61F 2002/30583* (2013.01); *A61F 2002/30589* (2013.01); *A61F 2002/30754* (2013.01); *A61B 17/1666* (2013.01); *A61B 17/1668* (2013.01); *A61B 17/686* (2013.01); *A61B 17/8872* (2013.01)
USPC .................................... 623/22.11; 623/16.11

(56) References Cited

U.S. PATENT DOCUMENTS

| | | |
|---|---|---|
| 5,997,582 A | 12/1999 | Weiss |
| 6,761,741 B2 | 7/2004 | Lesaka |
| 2004/0230309 A1* | 11/2004 | DiMauro et al. ............ 623/17.12 |
| 2006/0085075 A1* | 4/2006 | McLeer ...................... 623/17.12 |
| 2007/0173946 A1* | 7/2007 | Bonutti ....................... 623/20.14 |
| 2009/0076605 A1 | 3/2009 | Linares |

* cited by examiner

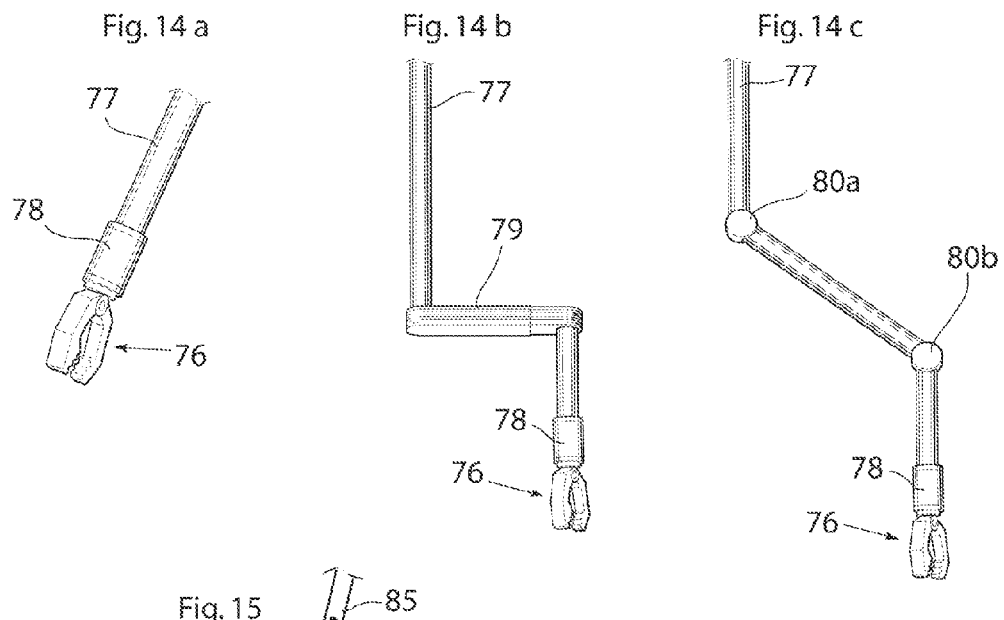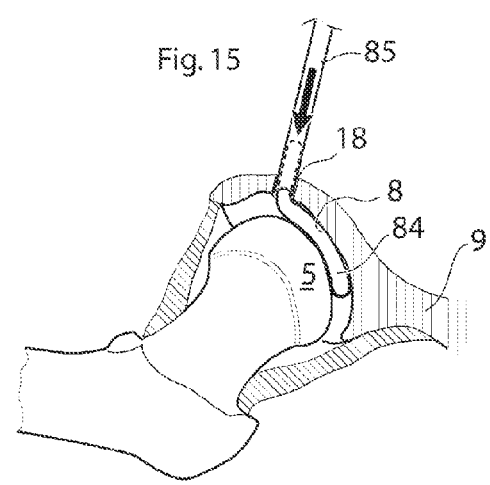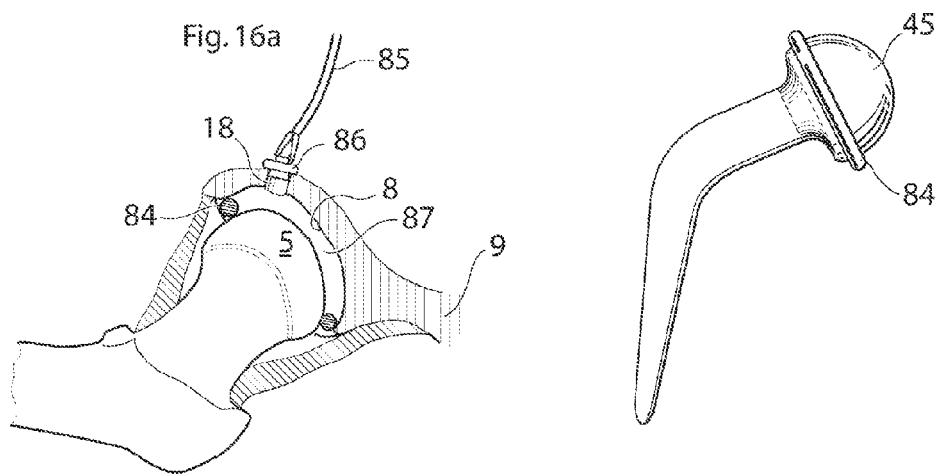

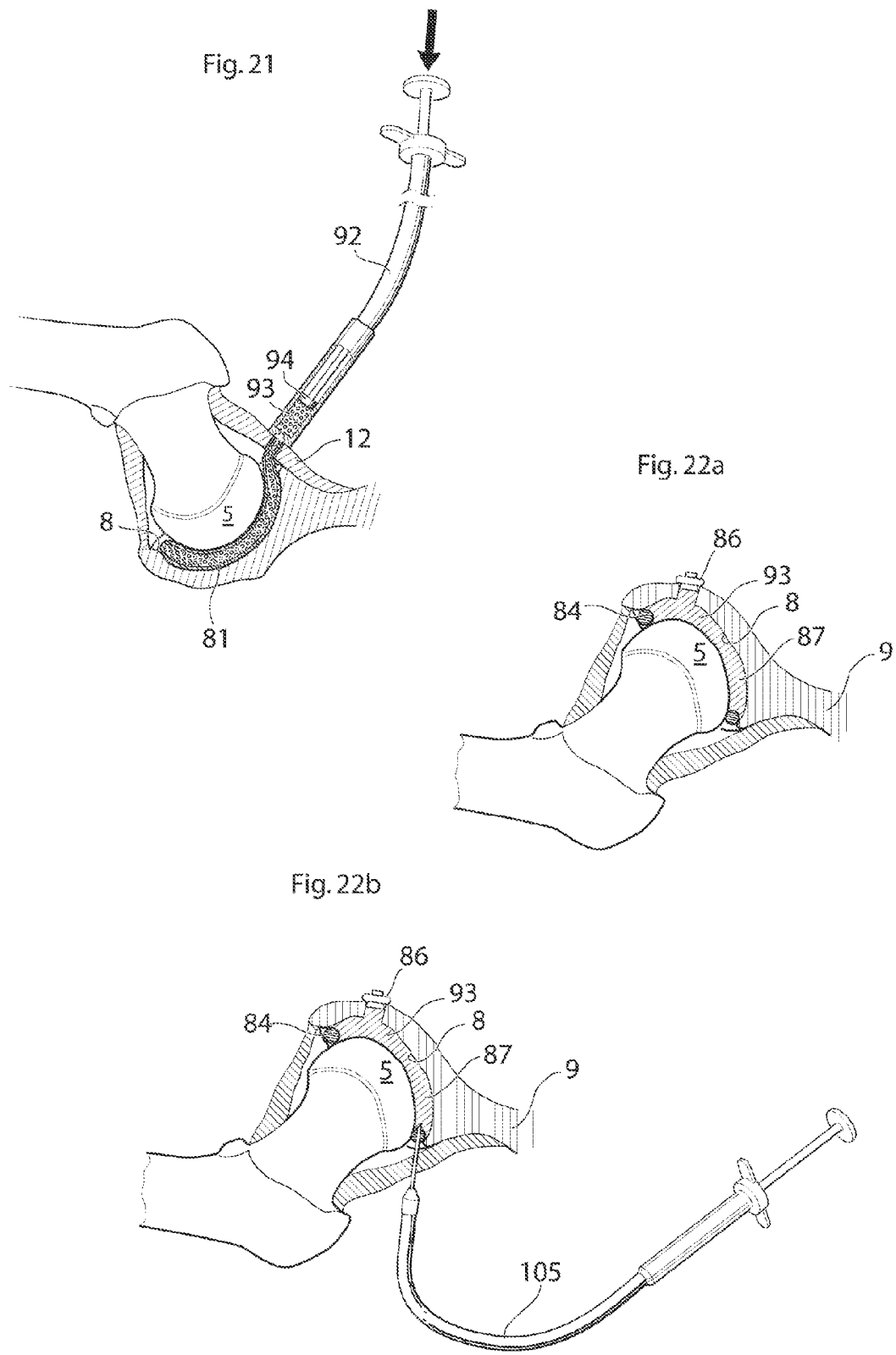

HIP JOINT DEVICE, SYSTEM AND METHOD

This application is the U.S. national phase of International Application No. PCT/SE2010/050820, filed 12 Jul. 2010, which designated the U.S. and claims the benefit of U.S. Provisional Nos. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device for use in a surgical or laparoscopic method of treating hip osteoarthritis in a human patient.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through a lateral incision in the hip and upper thigh and through, Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

SUMMARY

A medical device for treating hip joint osteoarthritis by providing a hip joint surface is provided. The hip joint comprises an acetabulum, being a part of the pelvic bone, comprising an acetabulum surface, and a caput femur, being a part of the femoral bone, comprising a caput femur surface. The medical device comprises a first sealing member adapted to be placed in the hip joint for creating a hollow space together with acetabulum, or an artificial replacement therefor, and caput femur, or an artificial replacement therefor. The first sealing member is further adapted to have a shape adapted to seal the hollow space for receiving, within said hollow space, a material for resurfacing at least one of the acetabulum surface and the caput femur surface.

According to one embodiment the medical device further comprises a second sealing member. The first and second sealing members thereby define a sealed hollow space together with the caput femur, or an artificial replacement therefor, and the acetabulum, or an artificial replacement therefor. Furthermore the first and second sealing members are adapted to make contact with the material when the hollow space receives material for resurfacing at least one of the acetabulum surface and the caput femur surface.

According to a proffered embodiment the material used in any of the embodiments herein is biocompatible. The material could also be adapted to be injected into contact with the first sealing member and adapted to transform from a fluid state to a solid state after the material has been injected into the provisional mould. The material could further be adapted to have a surface tolerating wear and pressure when the material is in a solid state.

According to one embodiment the medical device further comprises a second sealing member. The first and second sealing members define a sealed hollow space together with the caput femur or the artificial replacement for the caput femur, and the acetabulum or the artificial replacement for the acetabulum, and the first and second sealing members are adapted to make contact with the material when the hollow space receives the material for resurfacing at least one of the acetabulum surface and the caput femur surface.

According to one aspect of the embodiments herein the first sealing member comprises an opening adapted to receive a material for resurfacing at least one of the acetabulum surface and the caput femur surface. The material could be a biocompatible material which could be adapted to transform from a fluid state to a solid state after the material has been injected into a provisional mould. A bio compatible material creates a low level of immune response and thus limits the risk of the body rejecting the foreign material of the implant.

According to one embodiment the first sealing member define a sealed hollow space together with the artificial replacement for the caput femur and the acetabulum. The opening of the first sealing member is adapted to receive the material for resurfacing the at least one surface of the hip joint.

According to yet another embodiment the first sealing member define a sealed hollow space together with the acetabulum or the artificial replacement for the acetabulum, and the caput femur or the artificial replacement for the caput femur. The opening of the first sealing member could be adapted to receive the material for resurfacing at least one surface of the hip joint.

The first and/or second sealing members according to any of the embodiments herein could be adapted to be introduced into the hip joint through a hole in the pelvic bone, the femoral bone or the hip joint capsule.

According to one embodiment the first sealing member is adapted to be introduced into the hip joint through a hole, and the second sealing member is adapted to seal the hole.

The first and/or second sealing members according to any of the embodiments herein could be adapted to be resorbable or melt after having served its purpose as sealing member.

The first sealing member could be an integrated part of the artificial caput femur surface or the caput femur surface.

According to one embodiment the second sealing member could be adapted to connect to an injecting member adapted to inject material into said hollow space.

Injecting Member

According to one embodiment the medical device, further comprises an injecting member in connection with the first and/or second sealing member and adapted to inject material into the hollow space.

According to one embodiment the injecting member adapted to inject material into the hollow space comprises: at least one container, for containing material, a material injecting member in connection with at least one of said first, and said second sealing members, and a material driving member in connection with said material injecting member, for pushing the material through the injecting member.

An injecting members could further comprises a second container, and the first and second containers could be adapted to hold different fluids. The injecting members could further comprises a mixing unit adapted to mix said fluids contained in said at least two containers. One of the fluids could be adapted to act as catalyzing agent. The injecting member could be adapted to inject a material adapted to be hardened.

According to one embodiment the injecting member could be adapted to inject a material adapted to be hardened, for example by means of UV-light or a gas serving as catalyzing agent.

The injecting member adapted to inject material into the hollow space could be adapted to be bent, by means of a fixed angle or an adjustable angle.

System

A system for treating osteoarthritis in a hip joint is further provided, the hip joint comprises an acetabulum, being part of the pelvic bone, and a caput femur, being a part of the femoral bone. The system comprises: at least one sealing member adapted to be placed inside of the hip joint, said at least one sealing member defining a sealed hollow space together with the caput femur, or an artificial replacement therefor, and the acetabulum, or an artificial replacement therefor. Furthermore the system comprises a material adapted to be injected into the hollow space, the hollow space is adapted to receive material for resurfacing or replacing the carrying contacting surfaces of the hip joint, and an injecting member in connection with the at least one sealing member, The injecting member being adapted to inject material into the hollow space.

The at least one sealing member could be adapted to be resorbable and/or melt after having served its purpose as sealing member.

According to one embodiment the system is further adapted to keep the material, adapted to be injected into the hollow space, sterile for example using heat, radiation, an antibacterial substances and/or an antibacterial surface.

The at least one sealing member could comprise a polymer material, which could be a silicone based material, a latex based material and/or biocompatible material such as polyurethane.

Method

A surgical or arthroscopic method for resurfacing at least one surface of a hip joint of a human patient using a medical device is further provided. The method comprises the steps of: creating at least one hole passing into the hip joint, placing a first sealing member between the acetabulum surface and the caput femur surface, thereby creating a sealed hollow space between the acetabulum and the caput femur using the first sealing member, and injecting a material into the sealed hollow space, and thereby creating an artificial hip joint surface.

A surgical or arthroscopic method for resurfacing at least one surface of a hip joint of a human patient is further provided. The method comprises the steps of: creating at least one hole passing into the hip joint, dissecting and preparing the hip joint, introducing at least one artificial hip joint surface, comprising at least one of an artificial acetabulum surface and an artificial caput femur surface. The at least one artificial hip joint surface comprises a first sealing member. The method further comprises the steps of creating a sealed hollow space between the first sealing member and one of the acetabulum surface or the artificial acetabulum surface and one of the caput femur surface or the artificial caput femur surface, selecting at least one artificial hip joint surface, and injecting a material into the hollow space.

A surgical or arthroscopic method is further provided, at least one artificial hip joint surface further comprises a second sealing member. The step of creating a sealed hollow space also comprise the steps of: sealing the hole passing into the hip joint with the second sealing member, and the step of injecting a material into the hollow space, comprises injecting through the second sealing member.

The first sealing member could comprise an opening, and the step of injecting into the sealed hollow space could also comprise the steps of: injecting a material into the hollow space through the opening.

The step of injecting into said sealed hollow space could also comprise the steps of: injecting a material into said hollow space through the opening in the first sealing member. The step of injecting a material into said hollow space, could also comprise the step of creating an artificial hip joint surface, or creating an intermediate artificial hip joint surfaces placed between an artificial caput femur surface and an artificial acetabulum surface.

According to one embodiment of the method the step of creating at least one hole passing into the hip joint could further comprise the step of creating two or more holes, wherein at least one of the hole could be used for viewing with a camera through said hole, and at least on of said holes could be used for introducing a dissecting tool into the hip joint.

According to one embodiment the step of using one hole for introducing a circulating clear fluid into the hip joint, thus allowing a better view with said camera is performed.

According to one embodiments the method could further comprise the step of removing the sealing member, and the sealing member could be resorbed by the human body or melt after having served its purpose as sealing member.

The step of dissecting and preparing the hip joint, could further comprises the step of reaming the acetabulum and/or the caput femur. The step of dissecting and preparing the hip joint, could further comprise the step of reaming the acetabulum and/or the caput femur using a reamer, which could be expandable for insertion through a hole.

The method could further comprise the step of the material changing from a fluid state to a solid state after the injection in the hollow space, for creating a carrying surface. The surface could be a surface tolerating wear and pressure in a hip joint surface, when the material is in a solid state.

The method could further comprise the step of introducing the first sealing member into the hip joint through a hole in the pelvic bone, the femoral bone and/or the hip joint capsule. The second sealing member could be adapted to seal the hole.

The injecting could also be performed through a hole in the pelvic bone, the femoral bone and/or the hip joint capsule.

Furthermore a method of treating hip joint osteoarthritis in a human patient using a medical device providing an artificial hip joint surface is provided. The method comprising the steps of: placing the medical device inside of the hip joint, using the medical device as a sealing member during the injection of a fluid into the hip joint, hardening of the fluid inside of the hip joint, and the hardened fluid serving as an artificial hip joint surface.

ALTERNATIVE EMBODIMENT

According to yet another embodiment a medical device for treating hip joint osteoarthritis is provided. The medical device comprising at least one artificial hip joint surface, the hip joint comprising an acetabulum being a part of the pelvic bone, and a caput femur being a part of the femoral bone. The artificial hip joint surface is adapted to replace a carrying of; the acetabulum, with an artificial acetabulum surface, and/or the caput femur, with an artificial caput femur surface. At least one of the artificial hip joint surfaces comprises a first sealing member, the medical device is adapted to receive injected material into a sealed hollow space in the hip joint, the medical device being adapted to seal the hollow space, when placed in the hip joint. The hollow space is thereby being sealed by: acetabulum or an artificial acetabulum surface, and caput femur or an artificial caput femur surface. At least one of; the artificial acetabulum surface and the artificial caput femur surface is a part of the hollow space and comprising the first sealing member.

According to one embodiment the first sealing member is adapted to be inserted into the hip joint through a hole in any of: the pelvic bone, the femoral bone and the hip joint capsule. The first sealing member could further be adapted to be resorbable, and/or melt after having served its purpose as sealing member.

According to one embodiment the first sealing member comprises an injecting tube adapted to enable the injection of fluid through said first sealing member.

According to one embodiment, the system could further comprise at least two different fluids each adapted to be contained within one of said two containers, and wherein one of said two fluids is adapted to act as catalyzing agent.

According to one embodiment, the system could comprise a fluid adapted to be injected into the mould, wherein said fluid is adapted to cure and change from a fluid to fixed form. The fluid could for example be adapted to be cured by UV-light or by a gas serving as catalyzing agent.

According to yet another embodiment, the injecting member comprises at least one bent portion, which could be bent at an adjustable angle.

According to another embodiment, the system could further comprise a heating element adapted to heat said container for heating the fluid contained therein. The heating element could be adapted to heat said fluid to a temperature in the interval 40-60 degrees Celsius, or in the interval 60-90 degrees Celsius, or in the interval 90-200 degrees Celsius, or in the interval 200-400 degrees Celsius or more than 400 degrees Celsius.

According to another embodiment, the system further comprises a radiation source adapted to radiate said container for sterilizing the fluid contained therein.

According to yet another embodiment, the fluid could comprise at least one antibacterial substance, wherein said material adapted to be injected into said mould is held sterile by said at least one antibacterial substance. It is further more conceivable that the container has antibacterial inner surfaces, adapted to be in contact with said fluid.

The fluid could according to any of the embodiments herein be a fluid material having a melting point in the interval 40-60 degrees Celsius, or in the interval 60-90 degrees Celsius, or in the interval 90-200 degrees Celsius, or in the interval 200-400 degrees Celsius or more than 400 degrees Celsius.

According to yet another embodiments the fluid could comprise at least one material selected from the group consisting of: polytetrafluoroethylene, perfluoroalkoxy, fluorinated ethylene propylene, polyethylene, and acrylic polymer mixed with alumina trihydrate.

Please note that any embodiment or part of embodiment as well as any method or part of method could be combined in any way.

BRIEF DESCRIPTION OF DRAWINGS

The embodiments are now described, by way of example, with reference to the accompanying drawings, in which:

FIG. 14a shows an instrument for inserting a sealing member into a hip joint according to a first embodiment, FIG. 14b shows an instrument for inserting a sealing member into a hip joint according to a second embodiment, FIG. 14c shows an instrument for inserting a sealing member into a hip joint according to a third embodiment, FIG. 15 shows the insertion of a first sealing member into a hip joint, FIG. 16a shows the insertion of a second sealing member, FIG. 16b shows a sealing member being pre-mounted on an artificial caput femur surface, FIG. 21 shows the filling of a sealed area inside of the hip joint using an instrument that operates through the hip joint capsule, FIG. 22a shows a hip joint in section after a sealed area in the hip joint has been filled with a fluid, FIG. 22b shows a an injecting member injecting a fluid through a sealing member.

DETAILED DESCRIPTION

Figure 1:
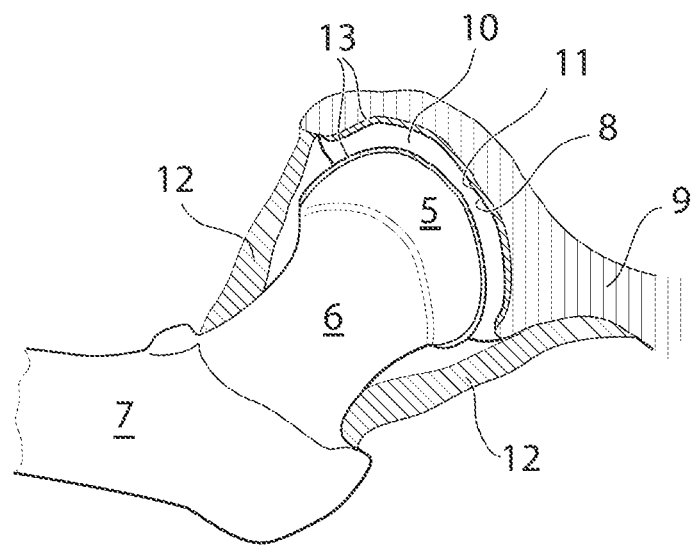
FIG. 1 shows the hip joint in section.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

Resorbable material is to be understood as a material which is adapted to resorbed by the human body after some time of implantation, and thus, at least partly, disappear from the place of implantation.

Biocompatible material is to be understood as being a material with low level of immune response. Biocompatible materials are sometimes also referred to as biomaterials.

FIG. 1 shows the hip joint of a human patient in section. The hip joint comprises a caput femur 5 placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
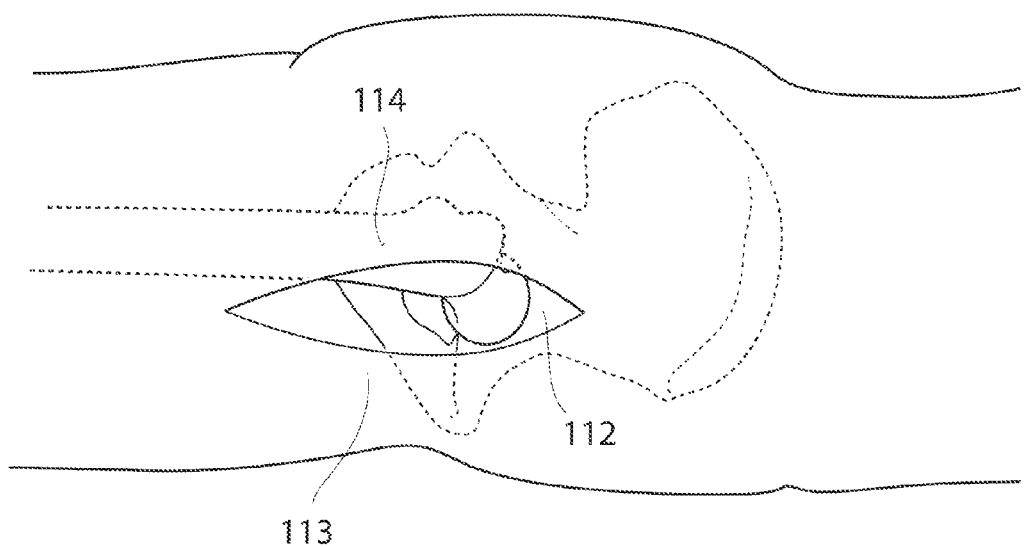
FIG. 2 shows a lateral view of a conventional hip joint surgery.

FIG. 2 shows a lateral view of a conventional hip joint surgery where an incision 112 is made in the tight 113 enabling the surgeon to reach the femur bone 7 on which the caput femur 5 is located. In a conventional hip joint surgery the hip joint is accessed through the hip joint capsule, which results in a large scar.

Figure 3:
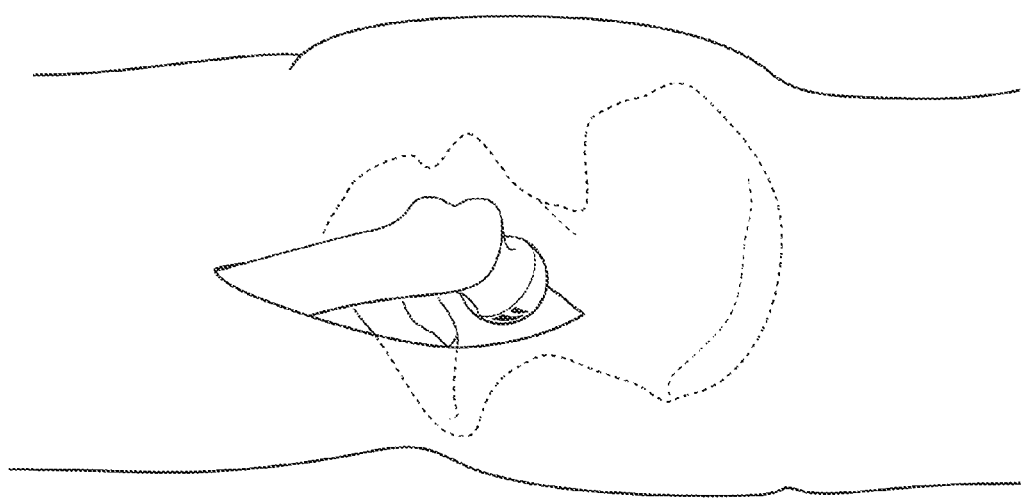
FIG. 3 shows an artificial caput femur being used in conventional surgery.

FIG. 3 shows the placing of an artificial caput femur surface 45 on the caput femur 5 in conventional surgery.

To enable the providing of material possible to use as bearing contacting surface in the hip joint the hip joint needs to be accessed. With reference to FIG. 1 this could be through a hole placed in the pelvic bone 9, the femoral bone 7 or the hip joint capsule 12.

Figure 4:
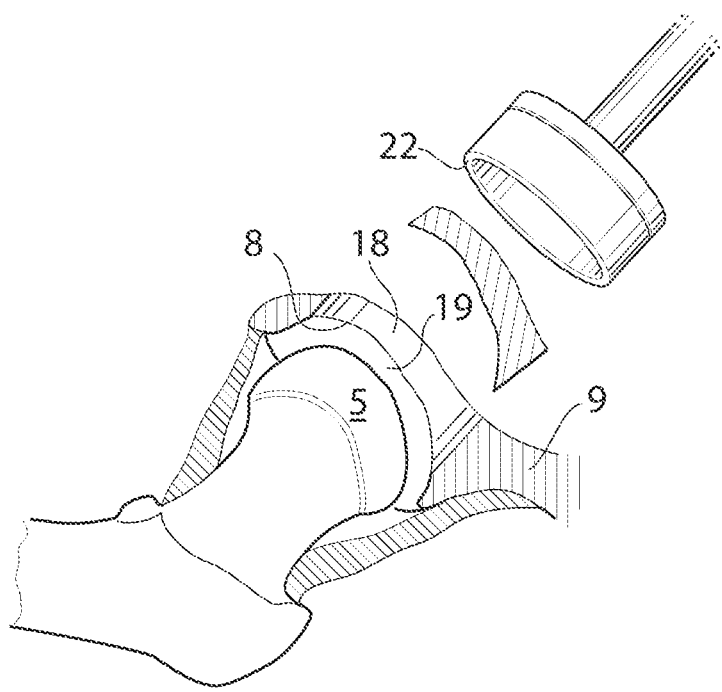
FIG. 4 shows the hip joint in section when a hole is created in the pelvic bone.

FIG. 4 shows the hole 18 in the pelvic bone 9 according to a first embodiment, the hole 18 is large which allows prosthesis to pass through said hole 18 in their full functional size.

Figure 5:
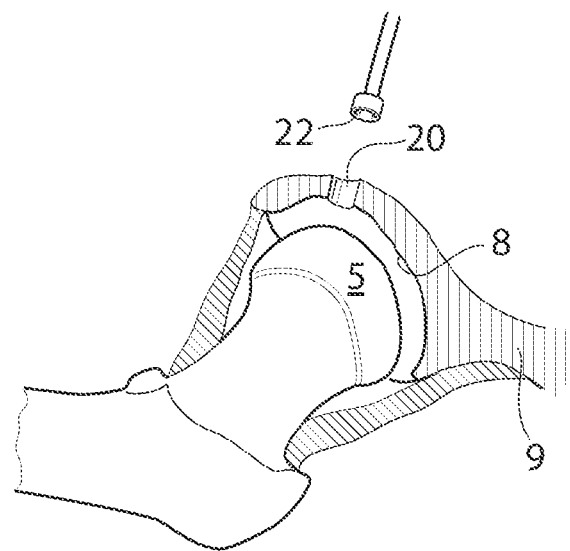
FIG. 5 shows the hip joint in section when a small hole is created in the pelvic bone.

FIG. 5 shows the hole 20 according to a second embodiment wherein the hole 20 created in a surgical or laparoscopic method is much smaller allowing the surgical instrument creating the hole to be smaller, and thus the incision and dissection performed in the human body.

Figure 6:
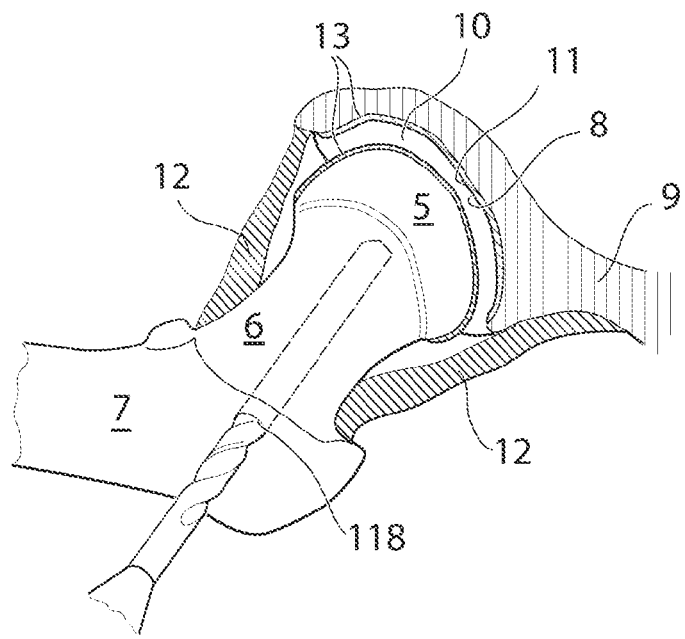
FIG. 6 shows the hip joint in section when a hole is created in the femur bone.

FIG. 6 shows the hip joint in section when creating a hole in the femur bone 7. The hole in the femur bone passes through the caput femur 5 into the hip joint and enables the surgeon to reach the hip joint.

Figure 7:
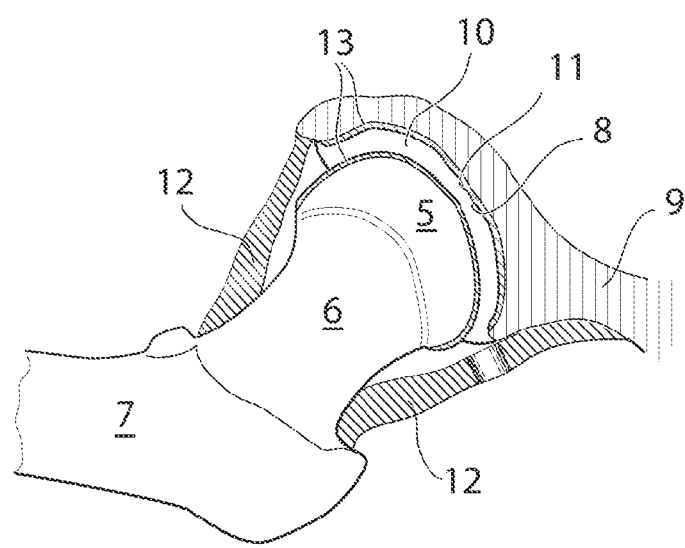
FIG. 7 shows the hip joint in section when a hole is created in the hip joint capsule.

FIG. 7 shows the hip joint in section when creating a hole in the hip joint capsule 12. The hole in the hip joint capsule passes into the hip joint and enables the surgeon to reach the hip joint.

Before the introduction of sealing members or material into the hip joint the hip joint surfaces could need to be prepared. This preparation could be performed by reaming the acetabulum and/or the caput femur surface.

Figure 8:
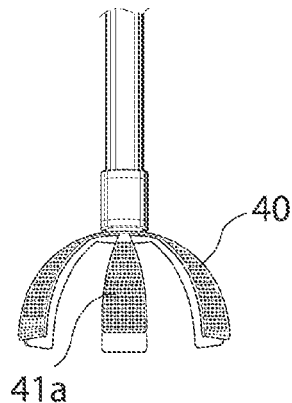
FIG. 8 shows the expandable reamer.

FIG. 8 shows a reamer according to a first embodiment wherein said reamer is expandable. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 9:
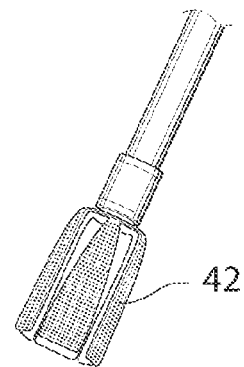
FIG. 9 shows the expandable reamer in its folded state.

FIG. 9 shows the expandable reamer according to the first embodiment wherein the reaming blades 40 can be folded towards a center of the semi-sphere that the expandable reamer produces in its expanded state, shown in FIG. 15. The folding of the reaming blades 40 enables the expandable reamer to be introduced into a hip joint through a hole smaller than the area possible to ream using said expandable reamer.

Figure 10:
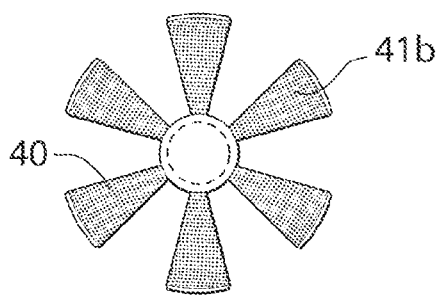
FIG. 10 shows the expandable reamer from underneath.

FIG. 10 shows the interior said of the expandable reamer with the reaming blades 40. In the embodiment when the expandable reamer is adapted to ream the caput femur said interior side of the at least one reaming blade 40 comprises a reaming surface 41b.

Figure 11:
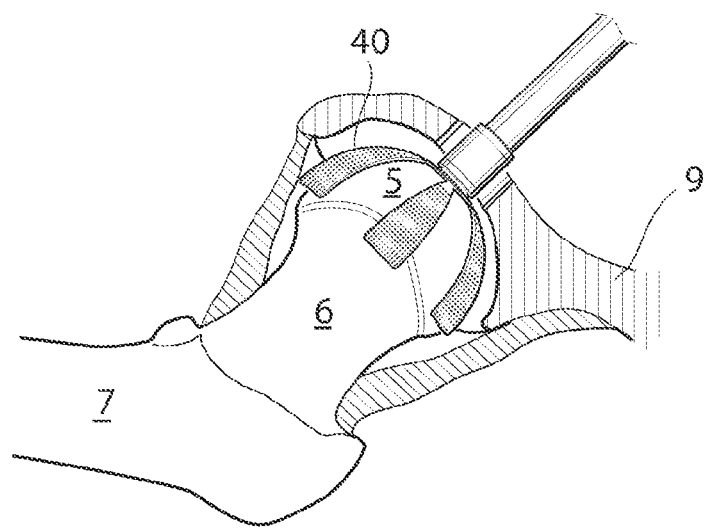
FIG. 11 shows the expandable reamer being used in the surgical or laparoscopic method.

FIG. 11 shows the expandable reamer according to any of the embodiments when reaming the acetabulum 8 and/or the caput femur 5. The reamer can be adapted to be operated manually or by means of a rotating, vibrating or oscillating operating device.

To get a view inside the hip joint it is conceivable that the surgeon can make a second hole in the pelvic bone, the femoral bone or the hip joint capsule to insert a camera.

Figure 12:
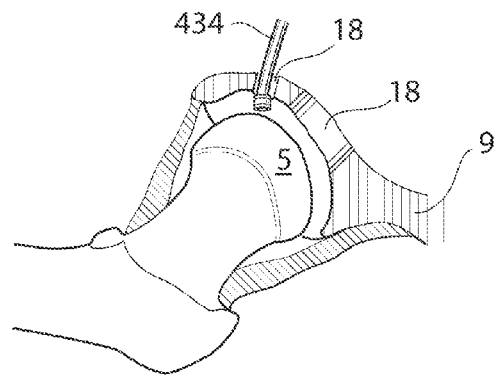
FIG. 12 shows the hip joint in section wherein a camera is placed into the hip joint.

FIG. 12 shows the hip joint in section wherein a second hole 18b in the pelvic bone 9 enables the surgeon to place a camera 34 into the hip joint, preferably used in a laparoscopic method.

Figure 13:
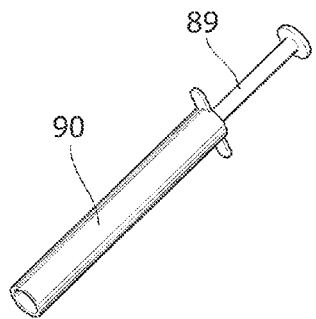
FIG. 13a shows an instrument for insertion of a sealing member into a hip joint.
FIG. 13b shows the instrument for insertion of a sealing member into a hip joint in section.
FIG. 13c shows the instrument for insertion of a sealing member into a hip joint according to a second embodiment.
Figure 13:
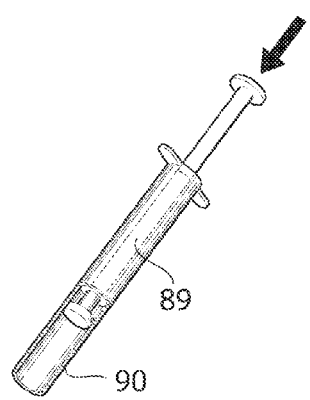
Figure 13:
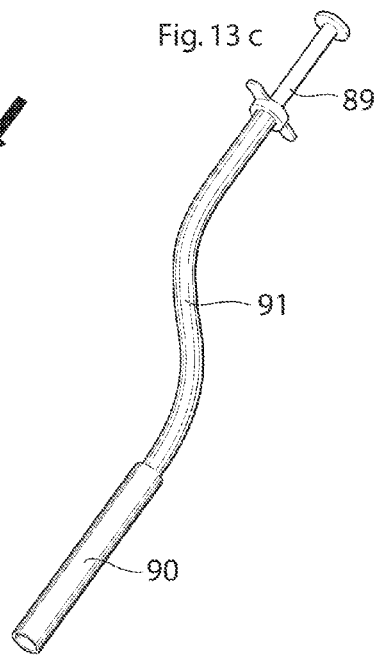

FIG. 13a shows an instrument for placing the first and/or second sealing member in the hip joint through a hole in the pelvic bone, the femur bone or the hip joint capsule. The instrument comprises a piston 89 for transporting the said first and/or second sealing member into the hip joint.

FIG. 13*b* shows a section of the surgical instrument comprising a tube like element 90 for housing of said first and/or second sealing member FIG. 13*c* shows the surgical instrument according to another embodiment in which the surgical instrument comprises a flexible or bent part 91 improving the reach of the surgical instrument. The surgical instrument according to any of the embodiments can be used to place said first or second sealing members inside of the hip joint in any of the ways described in the following embodiments.

FIG. 14*a* shows an instrument adapted to insert the first and/or second sealing member in the hip joint, according to a second embodiment. According to this embodiment the surgical instrument comprises a gripping portion 76 and a handling portion 77. According to the embodiments shown in FIGS. 14*a,b,c* the instrument further comprises a rotation element 78 that enables the gripping part 76 to rotate in relation to the handling part 77, however it is equally conceivable that the surgical instrument lacks this rotation element 78.

FIG. 14*b* shows the surgical instrument adapted to insert the first and/or second sealing member in the hip joint, according to a third embodiment. According to this embodiment the surgical instrument further comprises a parallel displaced section 79, which increases the reach of the instrument and facilitates the reaching of the hip joint through a hole in the pelvic bone, the femoral bone or the hip joint capsule.

FIG. 14*c* shows the surgical instrument adapted to insert the first and/or second sealing member in the hip joint, according to a third embodiment. According to this embodiment the surgical instrument further comprises two angle adjusting members 80*a,b*. The angle adjusting members could be adjustable for varying the angle of said gripping part 76 in relation to the handling portion 77, or fixed in an angle suitable for operating in a hip joint through a hole in the pelvic bone, the femur bone or the hip joint capsule.

FIG. 15 shows the hip joint in section wherein a first sealing member 84 is inserted through a hole 18 in the pelvic bone 9 using an instrument adapted therefor 85. The step of placing said first sealing member 84 can be performed in a surgical, or in a laparoscopic method.

FIG. 16*a* shows the hip joint in section wherein a second sealing member 86 is inserted through hole in the pelvic bone 9 in a surgical or a laparoscopic method. The first 84 and second 86 sealing members creates a sealed space 87 between the acetabulum 8 and the caput femur 5 adapted to be used as a mould for providing an artificial acetabulum 65 and/or a caput femur surface 45.

FIG. 16*b* shows an artificial caput femur surface 45 in an embodiment where the artificial caput femur surface comprises a pre-mounted first sealing member 84. The pre-mounted sealing member 84 is adapted to be placed in contact with the acetabulum, or an artificial replacement therefor. The artificial caput femur surface 45 with the sealing member 84 is adapted to be implanted into the hip joint of a patient and there create a sealed hollow space, adapted to receive a material, together with the acetabulum, or an artificial replacement therefor. The sealing member could be attached to the caput femur surface using an adhesive or the shape of the artificial caput femur surface 45.

Figure 17:
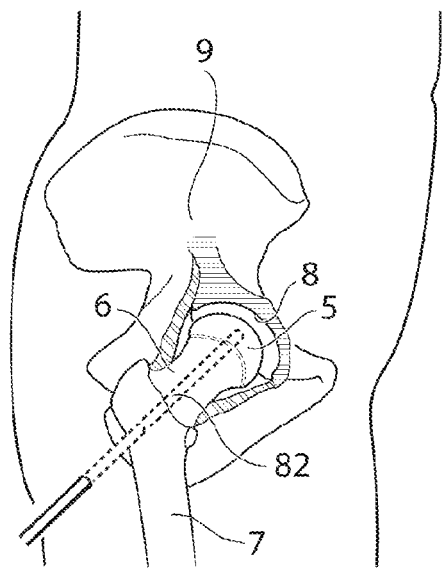
FIG. 17a shows the creation of a hole in the femur bone.
FIG. 17b shows an instrument able to introduce a sealing member into a hip joint through the femur bone.
FIG. 17c shows the placing of a sealing member inside of the hip joint using an instrument that operates through the femur bone.
Figure 17:
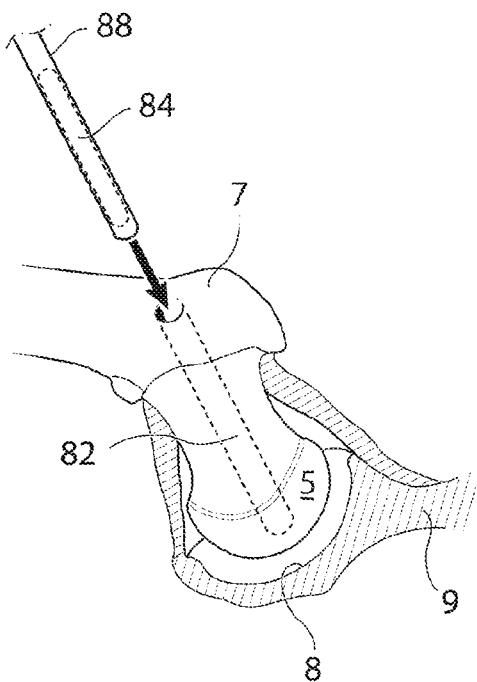
Figure 17:
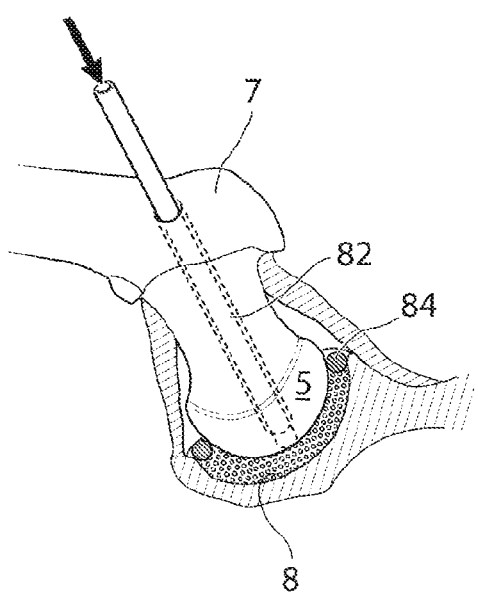

FIGS. 17*a,b,c* shows an alternative approach to placing said first sealing member 84 in the hip joint of a human patient. Said alternative approach comprises the steps of creating a hole 82 in the femur bone 7 following a length axis of the collum femur 6, as shown in FIG. 17*a*, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the first sealing member 84 is inserted into the hip joint through the hole 82 using a surgical instrument 88 adapted therefor, as shown in FIG. 17*c*. This approach could also be used for placing a second sealing member 86 in pelvic bone 9 or the femur bone 7 through the hole 82 in the femur bone 7.

Figure 18:
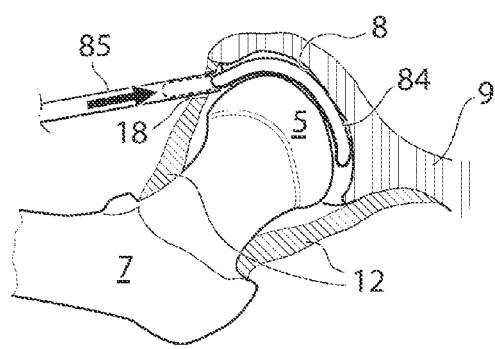
FIG. 18 shows the placing of a sealing member inside of the hip joint using an instrument that operates through the hip joint capsule.

FIG. 18 shows a third approach to the placing of a first sealing member 84 inside of the hip joint. According to this approach the first sealing 84 member is placed in the hip joint through the hip joint capsule 12.

It is furthermore conceivable that the first sealing member 84 is placed in the hip joint using any of the approaches above, whereas the second sealing member 86 is placed in the hip joint using another of the approaches above.

Figure 19:
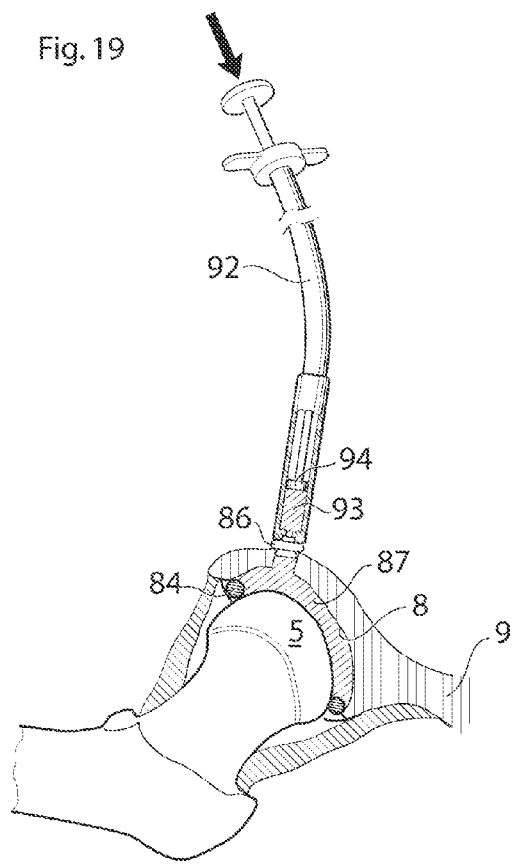
FIG. 19 shows the filling of a sealed area inside of the hip joint using an instrument that operates through the pelvic bone.

FIG. 19 shows the hip joint in section wherein an injecting member 92 injects a fluid 93 into a sealed area 87 in the hip joint through a hole 18 in the pelvic bone 9 from the opposite side from acetabulum 8. Said sealed area 87, being sealed by a first 84 and second 86 sealing member. The injecting member 92 comprises a piston 94 that pushes said fluid 93 into the sealed area 87. Said fluid 93 is adapted to harden either through the use of a catalyzing agent or not. After said fluid 93 has hardened it is adapted to serve as a hip joint surface.

Figure 20:
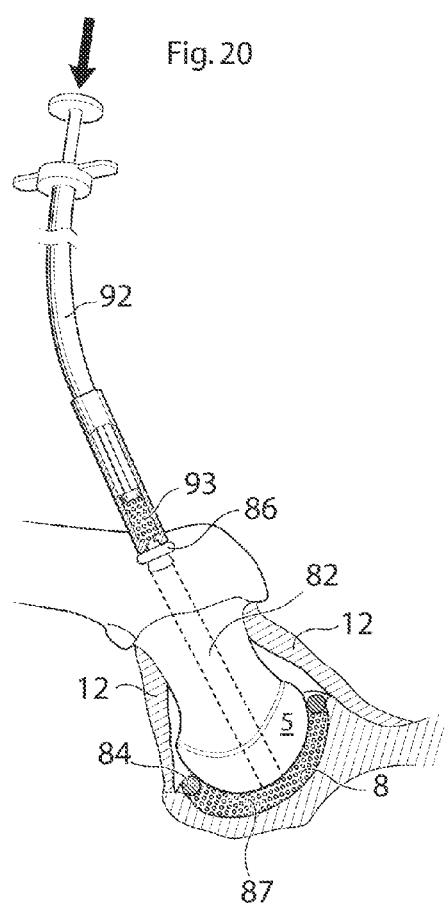
FIG. 20 shows the filling of a sealed area inside of the hip joint using an instrument that operates through the femur bone.

FIG. 20 shows the hip joint in section wherein an injecting member 92 injects a fluid 93 into a sealed area 87 according to the second approach. In this approach an injecting member 92 injects a fluid 93 into a sealed area 87 in the hip joint through a hole 82 in the femur bone 7. Said sealed area 87 being sealed by at least a first sealing member 84, and possibly a second sealing member 86. The injecting member 92 comprises a piston 94 that pushes said fluid 93 into the sealed area 87.

FIG. 21 shows the hip joint in section wherein an injecting member 92 injects a fluid 93 into a sealed area 87 according to the third approach. In this approach an injecting member 92 injects a fluid 93 into a sealed area 87 in the hip joint through the hip joint capsule 12.

FIG. 22*a* shows the sealed area 87, sealed by the first 84 and second 86 sealing member together with the caput femur 5 and the pelvic bone 9. A fluid adapted to harden 93 has been injected into said sealed area, and after the hardening of said fluid it provides at least one hip joint surface.

FIG. 22*b* shows an injecting member 105 injecting a fluid into a sealed area 87 in the hip joint, through a sealing member 84. The injecting member 105 comprises a needle for penetrating the sealing member 84, which preferably comprises a self sealing material, such as silicone. According to an alternative embodiment (not shown), the sealing member comprises a tube member penetrating the sealing member, through which the material can be injected. The tube member could be adapted to be made of the same material as the sealing member and reach from the area of the hip joint and to the outside of the body, where it could be connected to an injecting member. The tube member could be made of a resorbable material, or a material adapted to melt.

Figure 23:
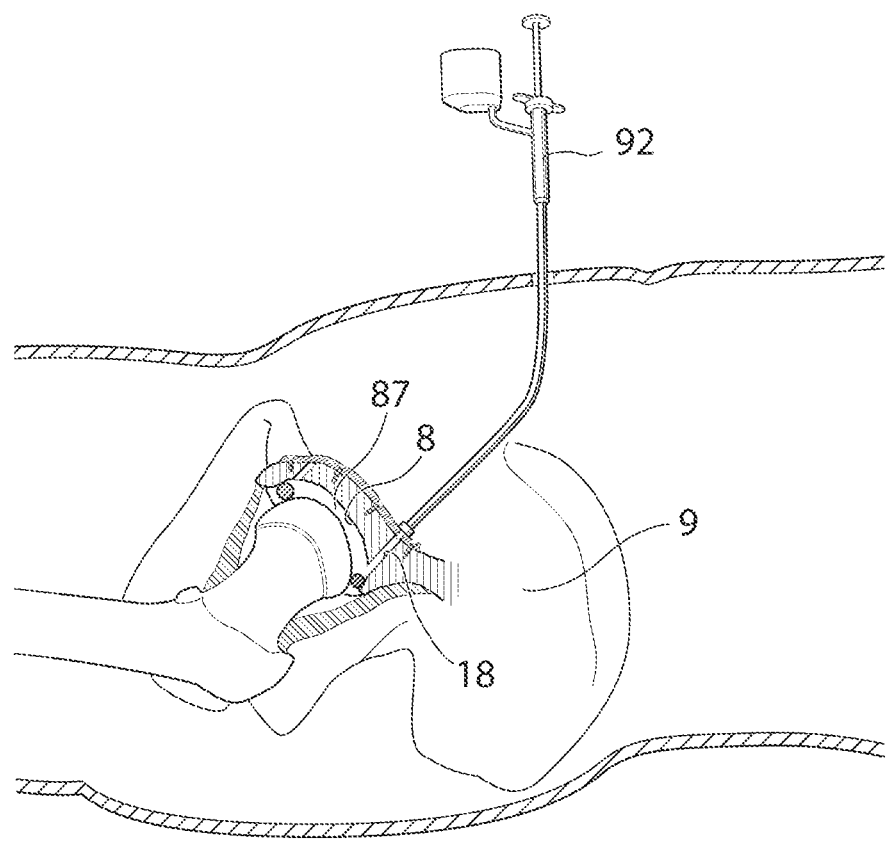
FIG. 23 shows the injection of fluid into an area of the hip joint.

FIG. 23 shows a lateral section of the human body wherein an injecting member 92 injects a fluid into a sealed area 87 in the hip joint through a hole 18 in the pelvic bone 9 from the opposite side from acetabulum 8.

Figure 24:
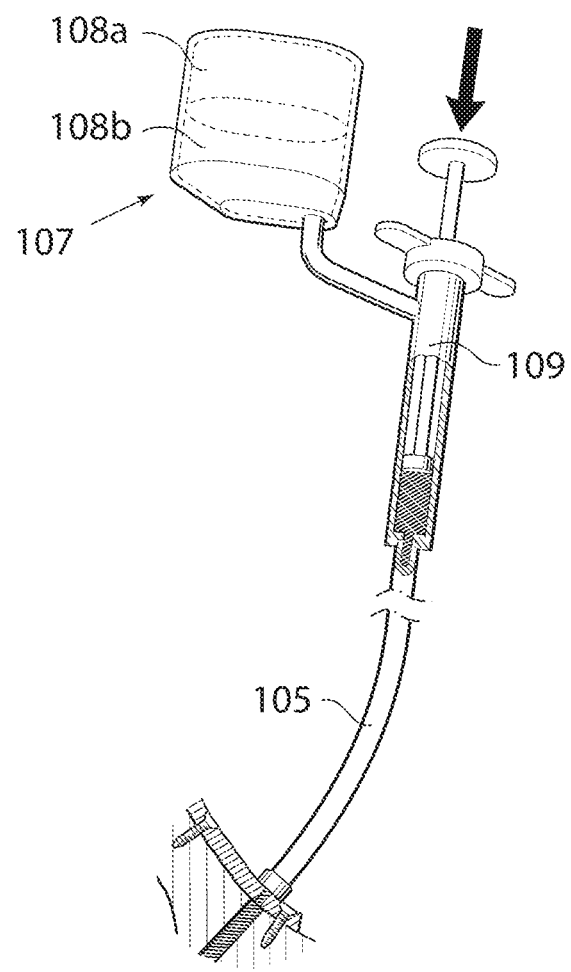
FIG. 24 shows an injecting member in further detail.

FIG. 24 shows the injecting member 105 according to any of the embodiments above, adapted to inject fluid 93 into a sealed area 87 or a connecting area between the pelvic bone 9 and a prosthetic part, the pelvic bone 9 and a bone plug 31 or the caput femur 5 and a prosthetic part. Said injecting member comprises a container 107 adapted to hold a fluid for injection. According to a first embodiment said container comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold or hot and according to a fourth embodiment (not shown) said container 107 is adapted to keep said fluid in a dark environment. Furthermore a combination of the above mentioned embodiments is conceivable.

According to any of the embodiments above said two fluids could be adapted to harden when mixed in which case one of the fluids could be a catalyzing agent. It is further more conceivable that one of said two fluids is a gas, such as nitrogen gas, which acts as a catalyzing agent when mixed with said first fluid. Said first, second or mixed fluid could also be adapted to harden by means of UV-light, thermic change or contact with a body fluid.

Figure 25:
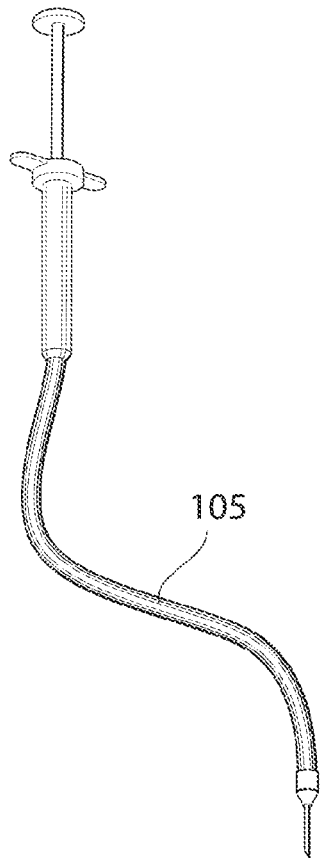
FIG. 25 shows an injecting member in further detail, according to a second embodiment.
Figure 26:
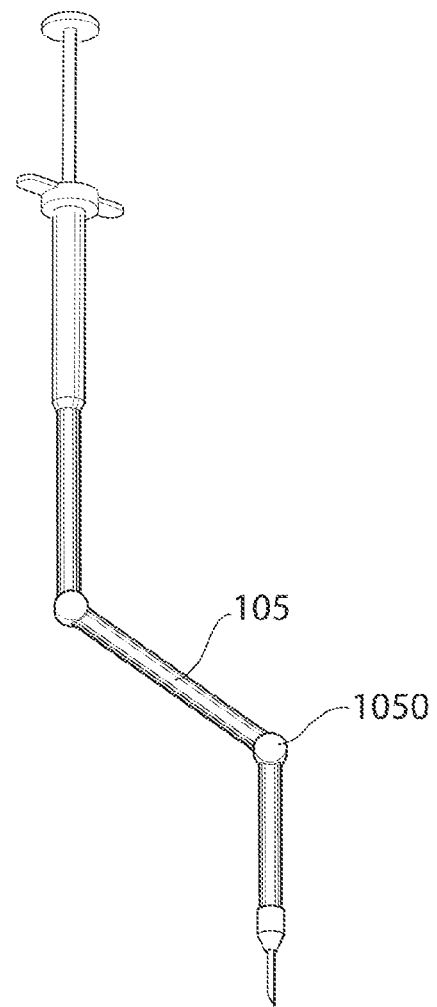
FIG. 26 shows an injecting member in further detail, according to a third embodiment.

FIG. 25 shows an injecting member 105 wherein the injecting member comprises a part or section adapted to bend. The instrument could be adapted to bend by means of said injecting member being flexible, shown in FIG. 25, or comprising at least one joint 1050, shown in FIG. 26.

Material

The sealed area could be filled with a solution comprising multiple fluids. According to one embodiment said first fluid is the same as said second fluid comprising a curable component, and the stabilization is initiated by adding a polymerization initiator, a catalyst, by subjecting the fluid to radiation, or by subjecting said fluid to a change in temperature. In this embodiment, the sealed area is filled with a fluid comprising a curable component, which can be stabilized at a desired point in time. Various polymerization initiators and catalysts are well known to a person skilled in the art, and a suitable initiator or catalyst can be chosen when the monomer or monomers have been chosen. The radiation can be any one of ultraviolet, infrared, and x-ray, depending on the material injected. It is also conceived that the radiation takes place before the curable component is introduced into the device, initializing a polymerization which then continues and becomes complete inside the device. Said second fluid is for example a fluid having a melting point sufficiently above normal body temperature to become solid at body temperature, but not as high as to compromise the health of the patient when in molten form. A suitable temperature difference is contemplated to be at least about 4° C., preferably about 6° C. or higher.

Alternatively, said curable component is a component capable of changing from fluid to solid form when exposed to a gaseous component, and wherein said hydraulic device implanted in the body contains no gas.

The curable component is preferably a biocompatible component.

Further, in embodiments, the curable component and at least one chamber holding said component are preferably kept under sterile conditions. Consequently, one embodiment comprises the use of a sterile reservoir containing the curable component, and the method includes the steps of moving the sterile curable component from said reservoir into the sealed area under sterile conditions. Further, according to another embodiment, the curable component comprises two sterile substances and the method includes, before the introduction of said substances into the body, the step of mixing said substances under sterile conditions.

According to one embodiment, said polymer is a thixotropic gel.

In combination with any of the above, it is preferred that said polymer is a biocompatible polymer.

According to a specific embodiment, said polymer is chosen among polyhydroxy acid polymers and copolymers such as poly-L-lactide, poly-DL-lactide, polyglycolide, and polydioxanone.

In combination with any of the above embodiments, it is also contemplated that said polymer further comprises reinforcing particles. Said reinforcing particles are preferably chosen among biocompatible ceramic particles or fibres made up of calcium phosphates.

In another embodiment, optionally combined with any of the above, said composition further comprises a crosslinker or a polymerization initiator.

Similarly, optionally combined with any of the above, said composition also comprises a propellant. Useful propellants comprise, but are not limited to, compressed gases, such as compressed air, nitrogen, oxygen or noble gases; liquefied propellants such as liquefied propane, isobutene, n-butane or a mixture thereof, dimethyl ether; or chlorofluorocarbons.

Examples of suitable biocompatible polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules (i.e. biopolymers such as collagen, elastin, bioabsorbable starches and the like) and blends thereof. Aliphatic polyesters include but are not limited to homopolymers and copolymers of lactide (which includes lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonate) include those described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in "Journal of Biomaterials Research", Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include those mentioned in U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and epsilon-caprolactone described inter alia by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form HOOC—C6H4—O—(CH2)m-O—C6H4-COOH where m is an integer in the range of from 2 to 8 and copolymers thereof with aliphatic alpha-omega diacids of up to 12 carbons.

Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference).

The term "biocompatible" is defined as the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimizing the clinically relevant performance of that therapy (David F. Williams "On the mechanisms of biocompatibility" Biomaterials, Volume 29, Issue 20, July 2008, Pages 2941-2953).

Please note that any embodiment or part of embodiment as well as any method or part of method could be combined in any way. All examples herein should be seen as part of the general description and therefore possible to combine in any way in general terms.

The invention claimed is:

1. A medical device for treating hip joint osteoarthritis by assisting in the injection of an artificial hip joint surface onto the natural hip joint surface or a surgically modified natural hip joint surface, wherein said medical device comprises a first sealing member adapted to be placed in the hip joint for creating a hollow space together with the acetabulum, or an artificial replacement therefor, and the caput femur, or an artificial replacement therefor, and a separate second sealing member adapted to seal a hole in bone, wherein said first sealing member has a substantially ring shaped body adapted to encircle said hollow space such that said hollow space is confined by the surfaces of the acetabulum, or an artificial replacement therefor, and the surface of the caput femur, or an artificial replacement therefor, adapted for receiving, within said hollow space, a material for resurfacing at least one of the acetabulum and the caput femur.

2. The medical device according to claim 1, further comprising a biocompatible material adapted to be injected into contact with said first sealing member, and wherein said biocompatible material is adapted to transform from a fluid state to a solid state after said material has been injected into said provisional mould, and wherein said material is adapted to have a surface tolerating wear and pressure when said material is in said solid state.

3. The medical device according to claim 1, wherein said medical device further comprises a second sealing member; wherein said first and second sealing members are adapted to define a sealed hollow space together with said artificial replacement for the caput femur, and the acetabulum, and
wherein said first and second sealing members are adapted to make contact with a material when said hollow space receives said material for resurfacing at least one of the acetabulum surface and the caput femur surface.

4. The medical device according to claim 1, wherein said medical device further comprises a second sealing member; wherein said first and second sealing members are adapted to define a sealed hollow space together with the caput femur, and said artificial replacement for the acetabulum, and
wherein said first and second sealing members are adapted to make contact with a material when said hollow space receives said material for resurfacing at least one of the acetabulum surface and the caput femur surface.

5. The medical device according to claim 1, wherein said medical device further comprises a second sealing member; wherein said first and second sealing members are adapted to define a sealed hollow space together with said artificial replacement for the caput femur, and said artificial replacement for the acetabulum, and
wherein said first and second sealing members are adapted to make contact with a material when said hollow space receives said material for resurfacing at least one of the acetabulum surface and the caput femur surface.

6. The medical device according to claim 1, wherein said first sealing member comprises an opening adapted to receive a material for resurfacing at least one of the acetabulum surface and the caput femur surface.

7. The medical device according to claim 6, further comprising a biocompatible material being adapted to transform from a fluid state to a solid state after said material has been injected into said hollow space, and wherein said material is adapted to have a surface tolerating wear and pressure when said material is in said solid state.

8. The medical device according to claim 6, wherein said first sealing member is adapted to define a sealed hollow space together with said artificial replacement for the caput femur, and the acetabulum, and wherein said opening of said first sealing member is adapted to receive said material for resurfacing said at least one surface of the hip joint.

9. The medical device according to claim 6, wherein said first sealing member is adapted to define a sealed hollow space together with said artificial replacement for the acetabulum, and the caput femur, and wherein said opening of said first sealing member is adapted to receive said material for resurfacing said at least one surface of the hip joint.

10. The medical device according to claim 6, wherein said first sealing member is adapted to define a sealed hollow space together with said artificial replacement for the caput femur and said artificial replacement for the acetabulum, and wherein said opening of said first sealing member is adapted to receive said material, for creating an intermediate contacting surface between said artificial replacement for the caput femur and said artificial replacement for the acetabulum surface of the hip joint.

11. The medical device according to claim 1, wherein said first sealing member is adapted to be introduced into the hip joint through a hole in the pelvic bone.

12. The medical device according to claim 1, wherein said first sealing member is adapted to be introduced into the hip joint through a hole in the femoral bone.

13. The medical device according to claim 1, wherein said first sealing 10 member is adapted to be introduced into the hip joint through a hole in the hip joint capsule.

14. The medical device according to claim 1, wherein said first sealing member is adapted to be introduced into the hip joint through a hole, and wherein said second sealing member is adapted to seal said hole.

15. The medical device according to claim 1, wherein said first sealing member is adapted to be inserted into the hip joint through a hole in any of: the pelvic bone, the femoral bone and the hip joint capsule.

16. The medical device according to claim 1, wherein said first sealing member is adapted to be resorbable.

17. The medical device according to claim 1, wherein said first sealing member is adapted to melt after having served its purpose as sealing member.

18. The medical device according to claim 1, further comprising an artificial caput femur surface adapted to replace the surface of caput femur in a hip joint, wherein said first sealing member comprises an integrated part of said artificial caput femur surface.

19. The medical device according to claim 1, further comprising an artificial acetabulum surface adapted to replace the acetabulum surface, wherein said first sealing member comprises an integrated part of said artificial acetabulum surface.

* * * * *